United States Patent [19]

Deuel

[11] Patent Number: 5,332,669
[45] Date of Patent: Jul. 26, 1994

[54] PROSTATE-DERIVED MITOGEN

[75] Inventor: Thomas F. Deuel, St. Louis, Mo.

[73] Assignee: The Jewish Hospital of St. Louis, St. Louis, Mo.

[21] Appl. No.: 356,739

[22] Filed: May 24, 1989

Related U.S. Application Data

[63] Continuation-in-part of Ser. No. 815,685, Jan. 2, 1986, abandoned.

[51] Int. Cl.⁵ .................. C12N 5/00; A61K 37/36
[52] U.S. Cl. ................... 435/240.2; 530/399; 530/827; 530/854
[58] Field of Search .......... 435/240.2, 240.21, 240.23, 435/240.3; 530/399, 412, 417, 827, 854; 424/105; 514/21, 412, 418, 419, 850

[56] References Cited

PUBLICATIONS

Lawson et al., in The Prostatic Cell: Structure and Function, Part A, pp. 325-336, Alan R. Liss, Inc. N.Y., 1981.
Story et al., J. Urol. 130, 175-179 (1983).
Jacobs et al., Urol. 16, 428-491 (1980).
Simpson et al., Endocrinology 117, 1615-1620 (1985).
Harper et al., Nature 279, 160-162 (1979).
Harper et al., J. Neurochem. 34, 893-903 (1980).
Nishi et al., Biochem. Biophys. Res. Commun. 132, 1103-9 (1985).
Tackett et al., J. Urology, 133, 45-48 (1985).
Kris, et al., Biotechnology, Feb. 1985, pp. 135-140.
Gray et al., Nature 303, 722-725 (1983).
Scott et al., Science 221, 236-240 (1983).

Primary Examiner—Robert J. Hill, Jr,
Assistant Examiner—Marianne Parta Allen
Attorney, Agent, or Firm—Scott J. Meyer

[57] ABSTRACT

A prostate-derived growth factor is disclosed which has a mol. wt. of about 28 kDa, an NH₂-terminal sequence substantially identical to the NH₂-terminal sequence of the 6 kDa mature rat EGF, potent mitogenic activity against NRK cells without additional carboxy terminal processing to the mature 6 kDa EGF molecular species, cross-reacts with antisera against rat EGF and its mitogenic activity is blocked by anti-EGF receptor antisera.

2 Claims, 4 Drawing Sheets

Rat EGF    NSNTGCPPSYDGYCLNGGVCMYVESVDRYVCNCVIGYIGERCQHRDLR
Mouse EGF  NSYPGCPSSYDGYCLNGGVCMHIESLDSYTCNCVIGYSGDRCQTROLRWWELR
Human EGF  NSDSECPLSHDGYCHLDGVCMYIEALDKYACNCVVGYIGERCQYRDLKWWELR

PROSTATE-DERIVED MITOGEN

This invention was made in part with Government support under Grant No. HL 14147 awarded by the National Institutes of Health. The Government has certain rights to the invention.

CROSS-REFERENCE TO RELATED APPLICATION

This is a continuation-in-part of copending application Ser. No. 06/815,686, filed Jan. 2, 1986.

BACKGROUND OF THE INVENTION

This invention relates to a novel polypeptide growth factor and, more particularly, to a prostate-derived growth factor or mitogen.

In recent years a considerable number of growth factors derived from various animal cells have been isolated and characterized. Illustrative of these growth factors are nerve growth factor (NGF) which has been purified from several different cell sources, insulin-like growth factors (IGF-I and IGF-II), epidermal growth factor (EGF), fibroblast growth factor (FGF), platelet-derived growth factor (PDGF), endothelial cell growth factor (ECGF), somatomedins and transforming growth factors (TGF) derived from various tumors and virally transformed cells. For background information on these growth factors see, for example, the recent brief review article by Kris et al., *Biotechnology*, February 1985, pp. 135–140; and the comprehensive review in *Hormonal Proteins and peptides*, Ed. by Choh Hao Li, Vol. 12, "Growth Factors," Academic Press, 1984.

These growth factors, many of which are polypeptide hormone-like agents in structure, function to regulate the proliferation, differentiation and survival of animal cells. The isolation and characterization of these growth factors is of major importance for understanding the regulation of normal tissue specific DNA synthesis and cell division, as well as for understanding abnormal mechanisms of cell growth such as observed in atherosclerosis and in neoplasia. Growth factor activity in prostate glands may be especially important to characterize because benign prostatic hypertrophy and prostate cancer are common tumors in males and because prostatic cancer metastatic to bone is nearly unique in inducing osteoblasts to form new bone locally. Thus, trophic factors that are secreted by prostatic tissue may be important not only in the normal growth and differentiation of prostatic tissue but also as mediators of abnormal prostatic growth.

The concept of a trophic factor released by metastatic prostatic carcinoma cells in bone has been suggested heretofore. See Franks, *J. Path. Bact.* 72, 603–611 (1956); Cook et al, *J. Urol.* 99, 87–96 (1968); Galasko, *J. Bone Joint Surg.* 57B, 353–359 (1973); Warren et al, *Arch. Pathol.* 22, 139–160 (1936); and Rosai, in *Pathology*, eds. Anderson and Kissane, C. V. Mosby Co., St. Louis, 7th. ed., 1977, pp. 1978–2014. Growth factor activity in extracts of prostatic tissue have been previously demonstrated but not purified or characterized. See Lawson et al, in *The Prostatic Cell: Structure and Function*, Part A, eds. Murphy et al, Alan R. Liss, Inc., N.Y. 1981, pp. 325–336; Story et al, *J. Urol.* 130, 175–179 (1983 I); and Jacobs et al. *Urol.* 16, 488–491 (1980) A mRNA fraction in human prostatic cancer cells coding for a novel osteoblast-stimulating factor having a molecular weight of ~20,000 has recently been identified and associated with this activity by Simpson et al, *Endocrinology* 117, 1615–1620 (1985). Tackett et al, *J. Urology* 133, 45–48 (1985), disclose the presence of a mitogenic factor in expressed prostatic secretions in humans of about 30,000 daltons. However, no purification or characterization of the mitogenic factor is given.

In copending application Ser. No. 06/815,685, filed Jan. 2, 1986, a novel 25 kDa prostate-derived growth factor and a process for its preparation from rat prostate cells are disclosed. This growth factor, also designated as PrGF or PrDGF, was demonstrated to differ from previously described growth factors. The disclosure of said application was subsequently essentially published by Maehama et al, *Proc. Natl. Acad. Sci. USA* 83, 8162–8166 (1986).

BRIEF DESCRIPTION OF THE INVENTION

In accordance with the present invention a novel polypeptide growth factor has been isolated from prostate gland of rats and characterized as follows:

The prostate-derived growth factor or mitogen of this invention has an apparent molecular weight of about 25 kDa as determined by nonreduced sodium dodecylsulfate polyacrylamide gel electrophoresis (SDS-PAGE). It is a partially processed precursor of the 6 kDa mature rat epidermal growth factor (EGF) and has a substantially identical amino terminal sequence to rat EGF. The N-terminal amino acid sequence when considered with the amino acid composition analysis establishes that the 25 kDa EGF polypeptide is not a tetrameric complex of the 6 kDa mature EGF but an alternatively processed form of the pre-pro EGF polypeptide of 130 kDa reported by Gray et al., *Nature* 303, 722–725 (1983) and Scott et al., *Science* 221, 236–240 (1983). This novel 25 kDa mitogen is recognized by antisera against rat EGF and its activity is blocked by anti-EGF receptor antisera which blocks the active site of the receptor. It is a potent mitogen without additional carboxy terminal processing to the mature 6 kDa EGF molecular species.

The novel 25 kDa mitogen of this invention was previously purified to apparent homogeneity from rat prostates as disclosed in copending application Ser. No. 06/815,685, filed Jan. 2, 1986, and referred to as PrGF. The purified PrGF was demonstrated to have mitogenic activity toward normal rat kidney fibroblast cells (NRK). It induced the linear incorporation of [methyl-$^3$H]-thymidine into NRK cells over a concentration range of about 0–16 ng/ml. PrGF also stimulated the incorporation of [methyl-$^3$H]-thymidine into DNA of isolated osteoblasts from fetal rat calvaria, which indicated that PrGF may mediate the osteoblastic proliferation characteristic of metastatic prostatic cancer to bone.

The 25 kDa mitogen of this invention thus appears to be unique and is a potential and potent mediator of prostatic activities related to abnormal prostatic growth.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in connection with the accompanying drawings in which briefly:

FIG. 5A) Comparison of the primary sequence of human, rat, and mouse mature rat EGF. FIG. 5B) Organization of the mouse precursor EGF protein deduced by its cDNA sequence. The transmembrane domain was predicted by the hydrophobicity of the amino acids. The solid lines underneath represent protein products of the EGF gene product. A 25-kDa peptide could be formed by a cleavage at the mature rat EGF amino termini with no carboxy terminal cleavage.

The source material used for purifying PrGF illustrated by the results in one embodiment of the invention (Example I, below) was frozen rat prostates obtained commercially from Pel-Freez Biologicals (Rogers, Ark.). The initial material was homogenized and acid extracted with acetic acid and then purified 16,400 fold over the initial extracts by a series of purification steps. Thus, the acid extracted material was first subjected to ion exchange chromatography using SP-Sephadex® C-25 (sulphopropyl functional groups) and DEAE-Sephadex A-50 (diethylaminoethyl functional groups) columns. The active fractions were then concentrated by 70% ammonium sulfate precipitation followed by gel permeation chromatography with Sephadex G-75. The Sephadex (cross-linked dextran) based materials used above are well-known chromatographic materials commercially available from Pharmacia Fine Chemicals AB (Uppsala, Sweden).

The active fractions from the gel permeation chromatography were subjected to ion exchange HPLC using a TSK-DEAE-5-PW column commercially available from Bio-Rad (Richmond, Calif.). The active material from the reverse phase HPLC was then subjected to another HPLC step using a TSK-G2000SW gel permeation column commercially available from LKB (Bromma, Sweden) to produce the final 16,400 fold purified PrGF.

In accordance with other embodiments of the invention (Example II, below), the 25 kDa mitogen was isolated by three other independent purification protocols.

In order to illustrate specific preferred embodiments of the invention in greater detail, the following exemplary laboratory preparative work was carried out.

EXAMPLE I

Protein Purification

Nine hundred gm of rat prostate were homogenized at 4° C. in 1500 ml of 1.0 M acetic acid, centrifuged at $13,500 \times g$ for 30 min. and the precipitate re-extracted in 1500 ml of 1.0 M acetic acid. The pooled extracts were dialyzed against 10 mM ammonium acetate (pH 5.5). All subsequent purification steps were performed at 4° C. except for HPLC.

The acid extracts were loaded on a 4.5 cm×45 cm SP-Sephadex C-25 column (bed volume 700 ml) equilibrated with 10 mM ammonium acetate (pH 5.5) and eluted with 10 mM ammonium acetate (pH 5.5). The active fractions were pooled and adjusted to pH 7.0 with ammonium hydroxide and loaded on a 4.5 cm×30 cm DEAE-Sephadex A-50 column (bed volume 480 ml) equilibrated with 10 mM ammonium acetate (pH 7.0). The PrGF activity did not bind under these conditions and was eluted with the flow through fractions. The active fractions were pooled and concentrated with 70% ammonium sulfate and the precipitate was dialyzed against 1.0 M acetic acid and lyophilized.

The lyophilized sample was dissolved in 50 ml of 1.0 M acetic acid and loaded on a 5 cm×90 cm Sephadex G-75 column (fine, 200-400 mesh, bed volume 1550 ml) equilibrated with 1.0 M acetic acid. The column was eluted with 1.0 M acetic acid and the active fractions were pooled (250 ml), lyophilized, and 6.3 mg of the lyophilized sample (~33% of total protein) was dissolved in 5 ml of 10 mM ammonium acetate (pH 7.0) and loaded onto a Bio-Gel TSK-DEAE-5-PW column (21.5 mm×150 nun) equilibrated with 10 mM ammonium acetate (pH 7.0). The column was eluted with a linear ammonium acetate gradient (0.01-0.8 M) and fractions were assayed for biological activity.

The fractions corresponding to each of three activity peaks were collected and labeled I, II, and III in order of elution, dialyzed against 1.0 M acetic acid, and lyophilized.

Peak II samples from separate DEAE-HPLC runs were dissolved in 1.5 ml of 0.1% trifluoroacetic acid and loaded onto a 4.6 mm×150 mm $C_{18}$ column (particle size, 5 μm; pore size, 300 Å) equilibrated with 0.1% trifluoroacetic acid, and eluted with a linear gradient of 0-80% acetonitrile in 0.1% trifluoroacetic acid. The active fractions were pooled, dried by Speed Vac (Savant Instruments), dissolved in 100 μl of 50 mM sodium acetate (pH 5 5) 0.2 M NaCl, and injected into a 7.5 mm×300 mm TSK G2000 SW column (particle size, 10 μm) equilibrated with the same buffer. The column was eluted under isocratic conditions, fractions assayed for mitogenic activity, the active fractions pooled and dialyzed against 1.0 M acetic acid, and stored at −20° C.

Mitogenic Assays

The mitogenic activity of PrGF was assayed by incorporation of [methyl-$^3$H]-thymidine into acid-insoluble DNA of normal rat kidney (NRK) cells obtained from the American Type Culture Collection, Rockville, Md. NRK cells were maintained in Dulbecco's modified Eagle's medium (DMEM) (K.C. Biologicals) containing 10% fetal calf serum, 100 µg/ml penicillin, and 100 µg/ml streptomycin and split into 48-well cell culture cluster plates (Costar) for assay. Samples (1–20 µl) to be tested for mitogenic activity were diluted to 0.3 ml with phosphate buffered saline (PBS) (pH 7.3) and mixed with 1.5 ml of medium consisting of DMEM, 6% plasma derived serum (PDS), and [methyl-$^3$H]-thymidine (specific activity 62.5 mCi/mmol) and 0.75 ml of the sample media was used. The PDS was prepared from human platelet poor Plasma by the method of Vogel et al., *Proc. Natl. Acad. Sci. USA* 75, 2810–2814 (1978). After incubating the cells for 24 hrs, the sample medium was aspirated and the cells were washed twice with 0.8 ml of PBS and incubated with 0.8 ml of 10% trichloroacetic acid (TCA) for 15 min. The acid-insoluble material was washed with 0.8 ml of ether-ethanol (1:2) and dissolved in 0.3 ml of 0.4 N sodium hydroxide. 0.2 ml aliquots were mixed with 5 ml of Dimilume 30 (Packard Instrument Co., Inc., Downers Grove, Ill.) and counted in a liquid scintillation spectrometer. The activity from 0.3 ml PBS was used as background and subtracted from all other values. Assays were done in duplicate.

SDS-polyacrylamide Gel Electrophoresis

Fifteen percent SDS-PAGE was carried out according to the method of Laemmli, *Nature* 227, 680–685 (1970). Gels were stained with silver after fixation with 50% ethanol for 30 min in 100 ml of a solution of 0.8% silver nitrate, 0.2 M sodium hydroxide, and 0.22 M ammonium hydroxide. The gels were developed in 0.27 mM citric acid, 0.02% formaldehyde for 5–10 min and the reaction was stopped with 100 ml of 10% acetic acid.

To determine mitogenic activity in gels, 2 nun gel slices were incubated in 1 ml of 1.0 M acetic acid for 8–10 hrs, transferred into 2 ml of formic acid and incubated for another 8–10 hrs. The 70% formic acid extracts were dried and assayed for mitogenic activity.

Isoelectric Focusing

Isoelectric focusing was carried out in 7.5% polyacrylamide gels containing 2% ampholyte (Ampholine, pH 3.5–10; LKB) with 0.02 M phosphoric acid at the anode and 1.0 M sodium hydroxide at the cathode. The lyophilized samples were dissolved in 30% glycerol and 2% ampholyte and were run at a constant current of 50 mA until 250 V was reached and continued at 250 V until the dye marker (methyl red, pI 3.75) no longer migrated. The pH gradient was assayed after soaking 2 mm gel slices in 2 ml of HPLC-grade water for 8–10 hrs. Mitogenic activity was assayed as described above after soaking gel slices in 1.5 ml of 1.0 M acetic acid for 8–10 hrs, dialysis of each extract against 1.0 M acetic acid, and concentration of each extract by Speed Vac.

Amino Acid Analysis

Amino acid analyses were performed as adapted from Ishida et al *J. Chromatogr.* 204, 143–148 (1981), using the Waters Amino Acid Systems (Waters Associates, Milford, MA), and using 80 pMoles PrGF.

Stability Studies

Stability to boiling was tested after incubating 5 ng of purified PrGF dissolved with 0.1 ml PBS in boiling water for 5 min and rapid chilling on ice.

Reduced PrGF was tested after 10 ng of purified PrGF (in 0.5 ml PBS) was incubated in 0.1 M β-mercaptoethanol at 100° C. for 3 min, quick chilled on ice, and dialyzed against PBS. The control sample was treated in an identical manner (but without β-mercaptoethanol) and the percent activity of the treated sample to the untreated sample measured.

The effects of protease digestion were tested with 5 ng of purified PrGF incubated with either trypsin (50 or 100 µg/ml) or pronase (100 or 500 µg/ml) in 90 µl of PBS for 3 hrs at 37° C. The reactions were terminated with 10 µl of 1.0 M acetic acid and 3 min incubation in boiling water. Inactivated proteases were studied after incubating 100 µg/ml of trypsin or 500 µg/ml of pronase in 90 µl of PBS and 10 µl of 1.0 M acetic acid at 100° C. for 3 min.

Iodination of PrGF

Purified PrGF (2.7 µg) was iodinated by glucose oxidase-lactoperoxidase in the presence of 2 mCi carrier-free Na[$^{125}$I], using a radioiodination kit (New England Nuclear). Iodinated PrGF was extensively dialyzed against 10 mM sodium phosphate (pH 7.2) and stored at −20° C.

Protein Determination

Protein concentrations were determined by the method of Lowry, *J. Biol. Chem.* 193, 265–275 (1951), using bovine serum albumin as standard. The concentration of purified PrGF was determined by amino acid analysis.

The results of the above laboratory preparative work leading to the purification of the novel PrGF in one embodiment of this invention and demonstration of its biological activity are set forth in Tables 1 to 4, below, and the following detailed description of FIGS. 1 and 2.

Figure 1:
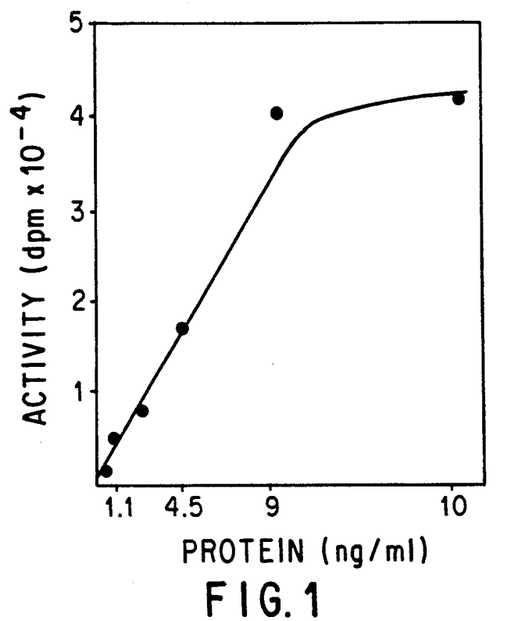
FIG. 1 is a graphical representation of the mitogenic dose response of purified PrGF on NRK cells in one embodiment of the invention, Example I, below.

FIG. 1

Mitogenic dose-response of purified PrGF

Incorporation of [methyl-$^3$H]-thymidine into DNA of NRK cells was measured with increasing concentrations of purified PrGF in 6% PDS-DMEM. The average background value without added PrGF (11,947 dpm) was subtracted from the values with PrGF. Full stimulation by 17% human serum was 76,724 dpm.

Figure 2:
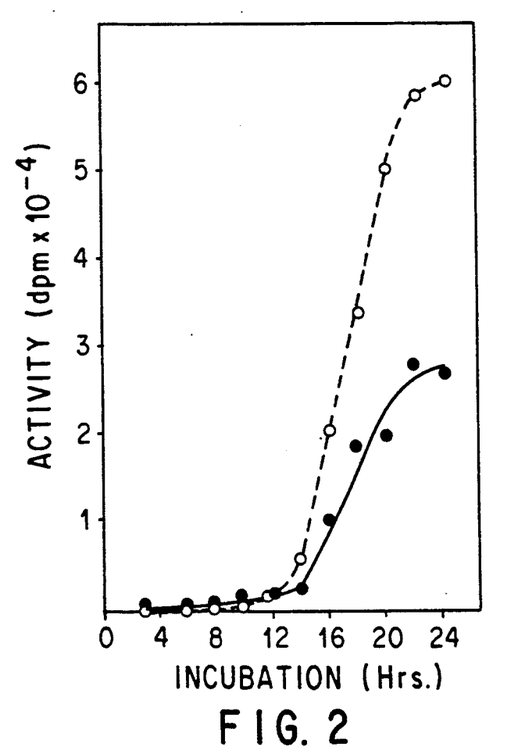
FIG. 2 is a graphical representation of the mitogenic time course of purified PrGF on NRK cells in the embodiment of FIG. 1.

FIG. 2

Mitogenic time course of purified PrGF on NRK cells

Confluent NRK cells were stimulated either with 5 ng/ml purified PrGF or with 17% human serum in 6% PDS-DMEM. A control assay of NRK cells used 6% PDS-DMEM alone. Incorporated [methyl-$^3$H]-thymidine into acid-precipitable DNA was measured and the control values subtracted from PrGF stimulated cells (●—●) or human serum stimulated cells (0—0).

The purification of the novel PrGF and demonstration of its mitogenic activity is thus evidenced from the above by explanation as follows:

Protein Purification

One molar acetic acid extracts of rat prostate were dialyzed against 10 mM ammonium acetate (pH 5.5). The mitogenic activity did not bind to a SP-Sephadex column but 64% of the mitogenic activity was recovered in the flow through fractions with a 12.5-fold purification. The fractions from SP-Sephadex column chromatography containing the activity were pooled and equilibrated to pH 7.0 and passed through a DEAE-Sephadex column with a recovery of 104% and an 87-fold purification.

The active fractions from DEAE-Sephadex were pooled, concentrated by ammonium sulfate precipitation (70% recovery, 97-fold purification) and the precipitate was resuspended in 1 M acetic acid (255 mg protein); the solubilized precipitate was fractionated on a Sephadex G-75 column and the active fractions collected. After lyophilization, the active fractions were loaded onto a DEAE-HPLC column, equilibrated with 10 mM ammonium acetate (pH 7.0), and eluted with a linear gradient (0.01–0.8 M ammonium acetate, pH 7.0). The elution profile of the DEAE-HPLC column demonstrated peaks of mitogenic activity. Peak II contained the largest amount of mitogenic activity and eluted at $\sim 0.50$ M ammonium acetate. Peak I eluted at $\sim 0.43$ M ammonium acetate and peak III at $\sim 0.56$ M, with recoveries of mitogenic activity of $\sim 56\%$, $\sim 22\%$, and $\sim 22\%$ respectively. The active peak II pool alone was used in subsequent purification.

The protein was then applied to a reverse phase $C_{18}$ HPLC column and a single activity peak eluted at $\sim 45\%$ acetonitrile, 0.1% trifluoroacetic acid, in a linear 0–80% acetonitrile gradient. The final purification was achieved using a TSK G2000 HPLC gel permeation column. A sharp single protein peak was found with near constant specific growth factor activity, resulting in $\sim 16,400$-fold purification. The results are summarized in Table below.

Amino Acid Analysis of PrGF

The amino acid composition of PrGF was analyzed and is set forth in Table 2, below. The amino acid composition is consistent with the pI determined. A peak was noted in the chromatographic analysis consistent with an amino sugar, suggesting that PrGF is a glycoprotein. This peak has not been further characterized.

Stability of PrGF to Heat, Reduction, and Proteases

The mitogenic activity of PrGF was completely retained after boiling purified PrGF (5 ng) for 5 min as shown in Table 3, below. Ten ng of purified PrGF was treated with 0.1 M $\beta$-mercaptoethanol for 3 min in boiling water. As shown in Table 3, PrGF lost essentially all mitogenic activity after treatment with $\beta$-mercaptoethanol. Two different proteases, trypsin and pronase, were tested with 5 $\mu$g of PrGF. Trypsin (100 $\mu$g/ml) reduced the mitogenic activity of PrGF to $\sim 61\%$ of original activity; pronase effectively destroyed all activity of PrGF. Neither inactivated trypsin (100 $\mu$g/ml) nor inactivated pronase (500 $\mu$g/ml) affected the biological activity of PrGF (Table 3).

In additional tests, PrGF was oxidized with sodium meta-periodate and reduced with [$^3$H]BH$_4$. Incorporation of [$^3$H] into purified PrGF was consistent with the labeling of carbohydrate, thereby further suggesting that PrGF is a glycoprotein. Purified PrGF was incubated also in cultures with preparations of osteoblasts from fetal rat calvaria. The purified growth factor stimulated the incorporation of [methyl-$^3$H]-thymidine into DNA of these isolated osteoblasts, providing initial evidence that PrGF may mediate the osteoblastic proliferation characteristic of metastatic prostatic cancer to bond.

TABLE 1

PURIFICATION OF PrGF FROM RAT PROSTATES

| Purification Step | Volume (ml) | Protein (mg) | Total Activity (dpm) | Yield (%) | (-fold) |
|---|---|---|---|---|---|
| Crude Extraction | 2700 | $6.99 \times 10^4$ | $2.32 \times 10^{10}$ | 100 | 1 |
| SP-Sephadex | 6800 | $2.06 \times 10^{10}$ | $8.54 \times 10^9$ | 37 | 12.5 |
| DEAE-Sephadex | 6150 | $3.08 \times 10^2$ | $8.89 \times 10^9$ | 38 | 87 |
| Ammonium Sulfate Precipitation | 50 | $2.55 \times 10^2$ | $6.45 \times 10^9$ | 28 | 93 |
| Sephadex G-75 | 256 | $1.89 \times 10^1$ | $7.21 \times 10^8$ | 3.1 | 115 |
| DEAE-HPLC peak II | 24 | $2.74 \times 10^{-1}$ | $4.04 \times 10^8$ | 1.7 | 4442 |
| (peak I)[a] | (20) | (—) | ($1.58 \times 10^8$) | (0.7) | (—) |
| (peak III)[b] | (16) | (—) | ($1.57 \times 10^8$) | (0.7) | (—) |
| $C_{18}$-HPLC | 10 | N.D.[c] | $3.16 \times 10^8$ | 1.4 | N.D. |
| TSK-2000 | 14 | $4.48 \times 10^{-2}$ | $2.44 \times 10^8$ | 1.1 | 16385 |

All values were based on 900 g of rat prostatic tissue used as starting material. Recoveries were calculated by assuming that all of the initial mitogenic activity was PrGF.
[a]mitogenic activity released at lower salt concentration
[b]mitogenic activity released at higher salt concentration
[c]N.D. = not determined
[d]protein was quantitated by amino acid analysis

TABLE 2

AMINO ACID COMPOSITION[a] OF PrGF

| | Moles/25 kDa | Normalized moles/mole PrGF |
|---|---|---|
| Asx | 28.89 | 29 |
| Threonine | 10.32 | 10 |
| Serine | 13.38 | 13 |
| Glx | 23.62 | 24 |
| Proline | 27.27 | 27 |
| Glycine | 33.16 | 33 |
| Alanine | 17.98 | 18 |
| Cysteine | N.D.[b] | — |
| Valine | 15.18 | 15 |
| Methionine | 2.00 | 2 |
| Isoleucine | 7.98 | 8 |
| Leucine | 12.92 | 13 |
| Tyrosine | 11.03 | 11 |
| Phenylalanine | 6.08 | 6 |
| Histidine | 9.31 | 9 |
| Lysine | 6.69 | 7 |
| Arginine | 8.99 | 9 |
| Tryptophan | N.D.[b] | — |

[a]Amino acid analysis was performed using the methods of Ishido, Y. Fujita, T., and Asai, K. (1981) J. Chromatogr 204, 143–148.
[b]N.D. = not determined
Asx = Asparagine or Aspartic acid
Glx = Glutamine or Glutamic acid

TABLE 3

| TYPE OF TREATMENT | BIOLOGICAL ACTIVITY[a] |
|---|---|
| Control | 100 |
| Heal (100° C., 5 min) | 111 |
| Reduction (0.1M, 2ME, 100° C., 3 min) | 11[b] |
| Proteases | |
| Trypsin (50 $\mu$g/ml) | 77 |
| Trypsin (100 $\mu$g/ml) | 61 |
| Inactivated Trypsin (100 $\mu$g/ml) | 94[c] |
| Pronase (100 $\mu$g/ml) | 1 |
| Pronase (500 $\mu$g/ml) | 1 |

TABLE 3-continued

| TYPE OF TREATMENT | BIOLOGICAL ACTIVITY[a] |
|---|---|
| Inactivated Pronase (500 μg/ml) | 131[c] |

Effect of heat, β-mercaptoethanol, and proteases on PrGF activity. Five ng of purified PrGF was used for all experiments except 10 ng of PrGF was used for treatment with β-mercaptoethanol (2ME). Details are described above.
[a]Results are expressed in percent of biological activity of control PrGF.
[b]Percent of biological activity of control PrGF, which was treated without β-mercaptoethanol but boiled and dialyzed the same way as the sample treated with β-mercaptoethanol.
[c]Inactivation of trypsin and pronase was performed by incubating enzymes in 0.1M acetic acid in boiling water for 3 minutes prior to addition of PrGF.

The properties of PrGF have been compared with properties of various well-known growth factors mentioned hereinbefore. As shown in Table 4, below, PrGF appears to be unique and not related to these previously described growth factors. Growth factors are abbreviated as above, except NSILA=nonsuppressible insulin-like activity per Rinderknecht and Humbel, *Proc. Natl. Acad. Sci. USA* 73, 2365-2369 (1976).

TABLE 4

| Growth Factor | Origin | M.W. k dalton | Di-sulfide bonds | P.I. | Stability Heat | Stability Acid |
|---|---|---|---|---|---|---|
| PDGF | Human Platelets | 28-31 | | 10.2 | stable | stable |
| EGF | Mouse Submaxillary Glands | 6 | + | 4.6 | stable | stable |
| FGF | | | | | | |
| acidic | Bovine Pituitary Glands, Brain | 17 | — | 5.8 | labile | labile |
| basic | | 15 | — | 8.5 | labile | labile |
| NGF | Mouse submandbular glands Guinea Pig, Rabbit Prostate Bovine seminal fluid | 13-15 | — | 8.5-1.0 | | |
| NSILA | Human Serum | 6 | — | 7.8-8.6 | stable | stable |
| ECGF | Bovine Brain | 75 | + | 4.6 | labile | labile |
| TGF | | | | | | |
| α | Transformed Cell Lines | 5-7 | — | | stable | stable |
| β | Transformed Cells Human Platelets, Placenta Bovine Kidney | 25 | + | 5.0 | stable | stable |
| PrGF* | Rat Prostate Glands | 25 | + | 5.0 | stable | stable |

*Tranforming Activity Absent

EXAMPLE II

Materials and Methods

Northern analysis. Whole cell and poly (A)+ RNA were purified from prostates of Sprague Dawley rats by the conventional methods of Chirgwin et al., *Biochemistry* 18, 5294 (1979), and Aviv and Leder, *Proc. Natl. Acad. Sci. USA* 69, 1408 (1972), respectively. Northern blot analyses were performed according to Maniatis et al., *Molecular Cloning: A Laboratory Manual*, pp. 202-203, Cold Spring Harbor Laboratory, (1983). The cDNAs encoding mEGF and EGF binding protein [Blaber et al., *Biochemistry* 26, 2742-2748 (1987)] were gifts of Drs. Graeme Bell (University of Chicago) and Ralph Bradshaw (University of California, Irvine), respectively.

Mitogen Assays. Mitogenic activity was assayed on NRK-49F cells (ATCC) by conventional procedure as described by Deuel et al., *J. Biol. Chem.* 256, 8896-8899 (1981). Antibody inhibition assays were performed by preincubating samples with antisera (1 hour at 4° C.) and adding them with $^3$H-thymidine media to serum-starved NRK cells. Mitogenic activity after 15% SDS PAGE [Laemli, *Nature* (London) 227 680-685 (1970)] was localized in 2 mm gel slices eluted with 70% formic acid in the cut gel assay described by Maehama et al., *Proc. Natl. Acad. Sci. USA* 83, 8162-8166 (1986) and in Example I, above.

Radioimmunoassay. EGF isolated as described below was labeled using an iodogen kit (New England Nuclear) for radioimmunoassay. Samples were incubated overnight at 4° C. with $^{125}$I-rat EGF (20,000 cpm, 250 μCi/ug) and 10 μl of a $10^{-3}$ dilution of anti-rat EGF antisera in a total volume of 300 μl with 0.1% BSA in phosphate buffered saline (PBS). Ten microliters of protein A-Sepharose were then added; 30 min later, the protein A-complex was separated by centrifugation, washed three times with 1.0 ml of BSA in PBS, and counted. The assay was linear from 0.01 ng to 1.0 ng EGF.

Antisera. EGF purified from rat submandibular glands by the conventional method of Schaudies and Savage *Comp. Biochem. Physiol.* 84 497-505 (1986), was further purified on C-18 and C-8 columns to obtain EGF of 99% purity, as judged by amino terminal sequencing. Purified rat EGF was coupled to keyhold limpet hemocyanin (KLH, ~1:10) and 200 μg of the conjugate emulsified with Freund's complete adjuvant was injected subcutaneously into rabbits. Seven days following monthly injections of 100 μg of rat EGF, animals were aseptically bled; the IgG fraction of serum was purified using a protein A Affiprep FPLC column (Bio-Rad). Affinity columns of EGF coupled to Affi-Gel 10 (Bio-Rad) were used to further purify the antisera. This affinity purified antisera was then linked to Affi-Gel 10 according to manufacturer's printed specification.

Protein Purification. The 25-kDa EGF-like polypeptide (described below) was purified by three separate methods from rat prostates (Pel Freez Biologicals and Charles Rivers).

Protocol 1) Seven hundred grams of rat prostates were homogenized in 1.0 M acetic acid and purified according to the methods of Maehama et al, supra, and as described in Example I, above. Further purification was achieved with a 10 cm Brownlee C-8 reversed-phase high performance liquid chromatography (RP-HPLC) column (Applied Biosystems Separation model 130 A, microbore) using a linear gradient from 0% to 50% acetonitrile in 0.1% trifluoroacetic acid (TFA) for elution. These samples also were analyzed by amino acid sequencing, cut gel assays, and antisera inhibition assays using both anti-rat EGF antisera and anti-mouse EGF receptor antisera (gift of Dr. G. Carpenter, Vanderbilt).

Protocol 2) Ten grams of rat prostates were homogenized at 4° C. in 20.0 ml of 20 mM tris, pH 7.0, with a Brinkman polytron, centrifuged at 10,000×g for 30 min, and filtered through a 0.45 μm filter. The precipitate was homogenized again and the combined supernatants were applied to a 1.0 ml anti-rat EGF immunoaffinity column (see above). After three sequential passages of homogenate through the column, the column was washed with 20.0 ml of PBS and eluted with 5.0 ml of 1.0 M propionic acid. The eluate sample was lyophilized, resuspended in 2.0 ml of 0.1% TFA, loaded onto a C-18 column, and eluted with a 60.0 ml linear gradient of 0–100% acetonitrile in 0.1% TFA. The active fractions were pooled, dried, and reapplied to the C-18 HPLC column. The active fractions were then applied to a C-8 HPLC column and eluted with a 60.0 ml linear gradient of 0–100% acetonitrile. The EGF-like mitogenic activity was used for amino acid sequence analysis and amino acid composition; cut gel assays were used to establish migration of mitogenic activity on SDS-PAGE.

Further purification of fractions not absorbed to the anti-EGF immunoaffinity column was performed after dialysis of samples against 20.0 ml tris (20 mM, pH 7.0), 0.1 M NaCl by chromatography on a 20.0 ml heparin-agarose FPLC column. Fractions were eluted at 0.8 M NaCl and 2.0 M NaCl in 20 mM tris, pH 7.0, dialyzed against 0.1M NaCl, 20 mM tris (pH 7.0) and tested for mitogenic activity. Cut gel assay and antisera inhibition assays were used to further characterize the mitogenic activity.

Protocol 3) One hundred grams of rat prostates were homogenized in 0.15 M ammonium sulfate buffer, and the pH was adjusted to 4.5. After two hours stirring, the sample was centrifuged for 30 min at 23,000×g. The supernatant was adjusted to pH 6.7, precipitated with 200 grams of $(NH_4)_2SO_4/L$, and centrifuged (23,000×g) for 30 min. An additional 250 grams of $(NH_4)_2SO_4/L$ was added to the supernatant and after centrifugation the precipitate was resuspended in 10.0 ml of 0.1 M sodium phosphate (pH 6.0), dialyzed against 0.1 M sodium phosphate (pH 6.0), loaded onto a 30×1.5 cm CM-Sephadex column, and eluted with 0.15 M NaCl and 0.6 M NaCl. The 0.6 M NaCl fraction, which contained all detectable mitogenic activity was dialyzed against 10.0 mM tris (pH 7.0), 0.6 M NaCl, and applied to a 20.0 ml heparin-agarose column (Sigma) and eluted with a linear gradient of 1.1 M to 2.0 M NaCl, 10 mM tris (pH 7.0). All the mitogenic activity was in the flow through (0.6 M NaCl) fractions and was analyzed by the cut gel assay and by inhibition with anti-rat EGF antisera.

Amino Acid Composition and Sequencing. Automated Edman degradation chemistry was used to determine the amino terminal protein sequence. An Applied Biosystems, Inc. Model 470A gas phase sequencer (Foster City, Calif.) was employed for the degradation [Hunkapiller et al, *Meth. Enzymol.* 91 399–413 1983)] using the standard sequencer cycle, 03c PTH. The respective phenylthiohydantoin (PTH) amino acids derivative were identified by reverse phase HPLC analysis in an on-line fashion employing an Applied Biosystems, Inc., Model 120A PTH Analyzer fitted with a Brownlee 2.1 mm I.D. PTH C-18 column.

Compositional analysis data was collected from 6 N HCl hydrolysates (vapor phase, 110° C., 24 hours) using Ninhydrin-based analysis performed on a Beckman 6300 High Performance Analyzer.

Results

Figure 3:
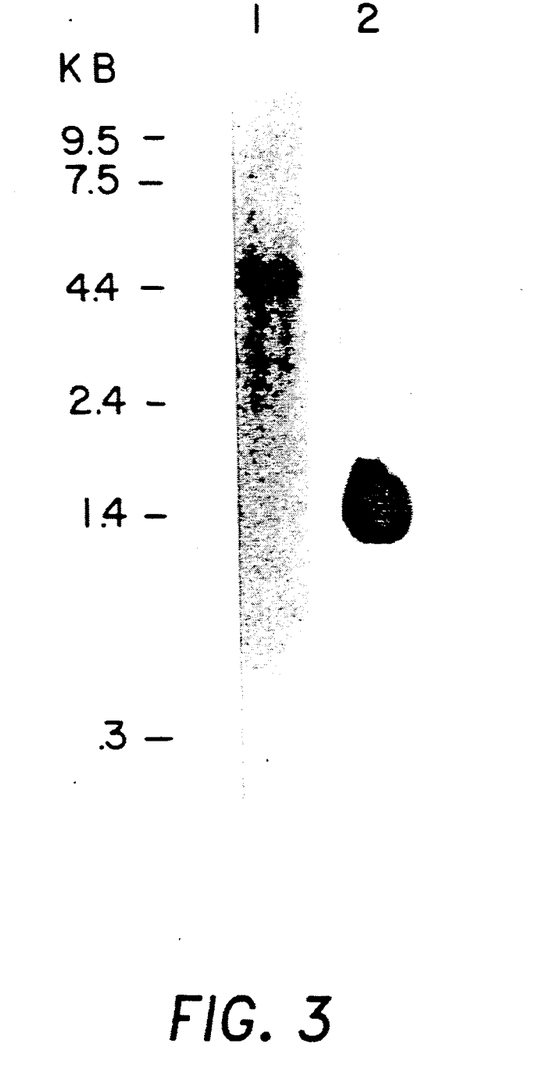
FIG. 3 shows the Northern blot of poly(A)+ RNA from rat prostates hybridized to probes for mouse EGF and EGF-binding protein. RNA was denatured by formamide and formaldehyde, and 5 micrograms per lane was electrophoresed on a 0.8% agarose gel, blotted to a nylon filter. Lane 1, RNA probed for EGF. Lane 2, RNA probed for EGF-binding protein.

The growth promoting activity of rat prostate extracts was compared to other rat tissues. Rat prostate was highly active in the standard mitogenic assay (see Materials and Methods, above). Only the submandibular gland had a higher specific activity (Table 5). To determine if a known growth factor was expressed in rat prostate, norther blots of poly(A)+ RNA from prostates were hybridized with cDNA probes of different growth factor genes. The EGF cDNA probe and the EGF-binding protein cDNA probes hybridized to 4.7 kBp and 1.5 kBp mRNA, respectively (FIG. 3). Other cDNA probes which also hybridized with poly(A)+ RNA from prostate included probes of the PDGF B-chain (4.2-kBp) and the HST oncogene (1.2-kBp). Because of the strong signal in the northern analysis with the cDNA probe from EGF, preincubation of the prostatic extract with anti-EGF antisera was tested; an ~60% inhibition of the mitogenic activity resulted (Table 5).

As mRNAs for both EGF and the EGF binding protein were detected in prostate poly(A)+ RNA and ~60% of the mitogenic activity in crude prostatic extracts was inhibited by anti-EGF antisera, an anti-EGF immunoaffinity column was used for purification of these EGF-like mitogens (Protocol 2, Methods). More than 50% of the mitogenic activity in crude extracts of prostate bound to the anti-EGF immunoaffinity column, correlating with the EGF-like activity estimated by inhibition of activity in crude prostatic extracts (Table 5). To further characterize the mitogenic activity not absorbed to the anti-EGF immunoaffinity column, the flow-through was absorbed to heparin-agarose (see Methods, above). Step elution using 0.1M NaCl, 0.8 M NaCl, and 2.0 M NaCl demonstrated that mitogenic activity was released equally within the 0.1M and 0.8 M NaCl fractions (Table 6). Essentially all the mitogenic activity in the 0.1 fraction was inhibited by anti-rat EGF antisera, suggesting that the immunoaffinity column had been overloaded or that other factors precluded binding of 100% of the EGF-like protein to the immunoaffinity column. No EGF-like activity was found in either the 0.8 M or 2.0 M NaCl fractions. Collectively, >80% of rat prostatic mitogenic activity was attributable to peptides immunologically similar to rat EGF. Levels of EGF-like mitogens in prostates were directly estimated using radioimmunoassay (see Methods, above); between 1–2 μg of EGF-like peptides per gm of tissue or, 35 ng of EGF-like peptides per mg of protein were found. The remaining ~20% of mitogenic activity in crude prostatic extracts appeared to be predominantly a heparin binding growth factor. It was eluted in the 0.8 M NaCl fraction from heparin-Sepharose and was not inhibited by either anti-rat EGF antisera or by anti-human PDGF antisera. Since the 2.0 M fraction would be expected to contain the previously described heparin binding growth factors, it seems likely that the prostatic activity is not basic or acidic FGF; its identity is not known.

Surprisingly, the predominant EGF-like species to elute from the EGF-immunoaffinity column was 25-kDa. However, a 6.0-kDa component on SDS-PAGE (FIG. 4) which co-migrated with mature EGF purified from rat submandibular glands was eluted also from the rat anti-EGF immunoaffinity column (data not shown). In order to establish the relationship the 25-kDa mitogenic peptide to the 25-kDa mitogenic polypeptide previously purified, the protocol previously describe by Maehama et al, supra., and in Example I, above, to isolate the 25-kDa mitogen (protocol 1 in Methods) was used in association with microbore reverse phase HPLC to achieve highest purity; a 25-kDa protein was obtained that was inhibited in antisera inhibition assays using anti-rat EGF antisera and anti-EGF receptor antisera (directed against the binding domain of the EGF receptor). This 25-kDa mitogen had a specific mitogenic activity 3-fold less than the mature 6-kDa form of rat EGF when compared in mitogenic assays and radioimmunoassays. Amino terminal amino acid sequencing demonstrated that this 25-kDa peptide had an amino terminal sequence identical to that of mature rat EGF.

Figure 5A:
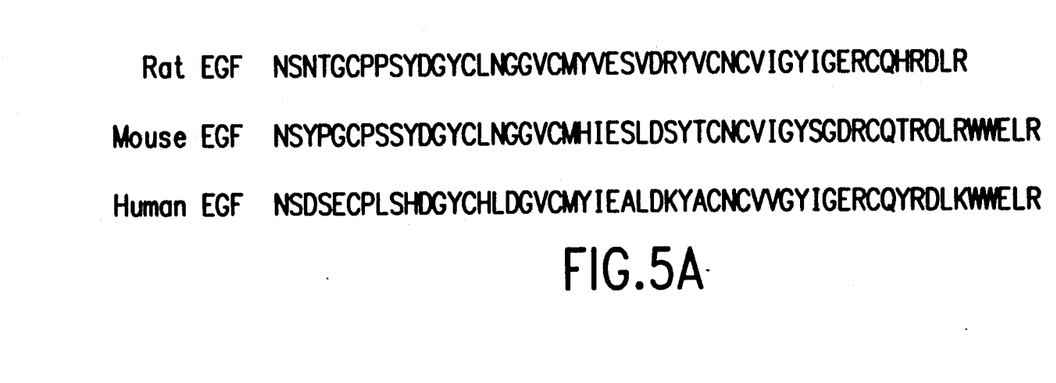
FIGS. 5A-B shows the primary sequence of mature rat EGF and a schematic representation of the cDNA for mouse pre-pro EGF.
Figure 5B:
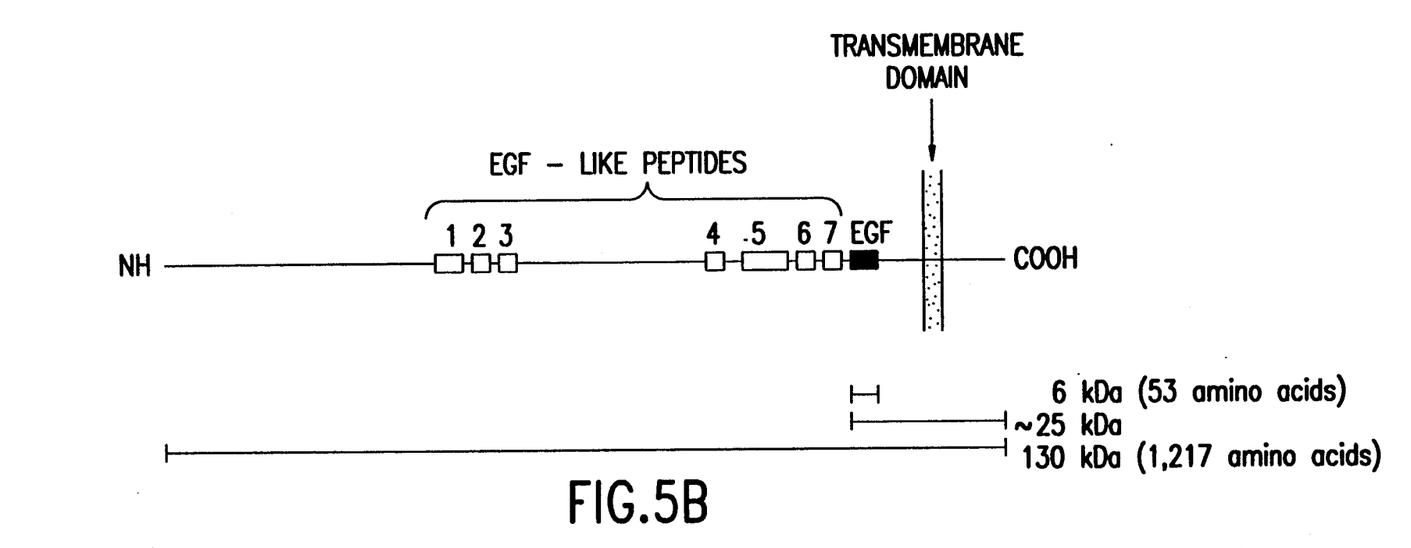

A third protocol adapted from the purification of basic FGF from bovine brain [Lobb and Fett, Biochemistry 23, 6925–6929 (1984); Gospodarowicz et al, J. Biol. Chem. 257, 12266–12276 (1982)] was then used to convincingly establish that the 25-kDa EGF-like protein was not an artifact of protocols 1 or 2, (see protocol 3 in Methods, above) (Table 7). The mitogen purified using the third protodol also was acid-stable and 25-kDa in size (FIG. 5), did not bind to heparin-agarose at 0.5 M NaCl, and was inhibited by anti-rat EGF antisera in an antisera inhibition assay (Table 8).

Isolation of the 25-kDa EGF-like mitogen from prostates using three separate purification protocols argued strongly against the possibility that this protein arose as an artifact of purification. As an additional control, mature rat EGF from submandibular glands (6.0-kDa) was then purified [Schaudies and Savage, supra.] and eluted as a 6-kDa species from the cut gel assay system eliminating the possibility that the 25-kDa EGF-like mitogen was the result of an artifactual estimate of molecular mass in the gel system used.

Figure 4:
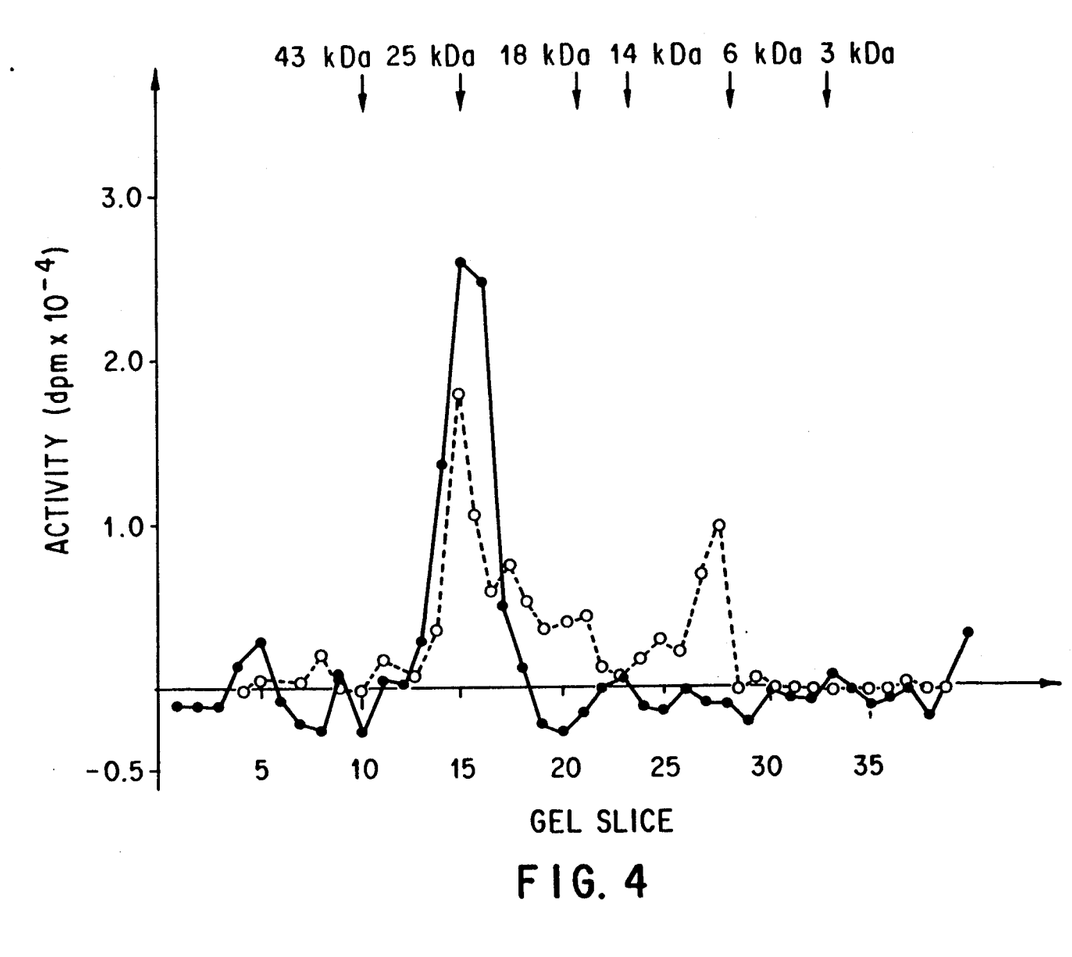
FIG. 4 shows the molecular weight of mitogens purified from rat prostates by protocols 2 and 3 in other embodiments of the invention, Example II, below. Sample containing $5 \times 10^5$ dpm of mitogenic activity was electrophoresed on a 15% SDS-PAGE. Mitogenic activity eluted from 2 mm gel slices was measured (Materials and Methods, Example II, below). The eluant of the EGF immunoaffinity column from protocol 2 (0—0) and the flow through fraction of the heparin agarose column from protocol 3 (●—●) were tested in a cut gel assay (Materials and Methods, Example II, below).

To definitively identify the 25-kDa EGF mitogen, additional mitogen was purified by immunoaffinity chromatography and with reverse-phase liquid chromatography (see Materials and Methods, above); recoveries of 50–60% were obtained. The mitogenic activity eluted in a single peak at ~30% acetonitrile, 0.1% TFA from a single C-18 column and contained both the 25-kDa and 6-kDa mitogens as detected by elution from gel slices (FIG. 4). The two mitogenically active polypeptides were not separated by additional chromatography on C-8 RP-HPLC (see Materials and Methods). Amino terminal amino acid sequencing was performed; 80% of the N-terminal amino acid sequence was identical to that of mature rat EGF. The remaining 20% had amino acid sequences identical to those of rat EGF minus the N-terminal glycine (des aa 1), and rat EGF minus the N-terminal three amino acids (glycine, alanine, alanine, des aa 3) (FIG. 5A). The purity of the samples sequenced was >95% with respect to EGF-like peptides.

Because there is only a single copy of the EGF gene, and because both the EGF peptides at 6-kDa and at 25-kDa shared identical amino terminal amino acid sequences and thus were the product of the EGF gene, two likely structures at the 25-kDa mitogenic polypeptide were considered. It was possible that the 25-kDa polypeptide is the carboxy-terminal portion of the 130-kDa pre-pro EGF, resulting from incomplete or differential processing (FIG. 5B). It was also possible that the 25-kDa was a tetramer of mature EGF, either naturally occurring in prostate or artifactually introduced during purification. To test these two possibilities, the amino acid compositions of the expected tetrameric aggregate of mature EGF and the predicted composition of the partially processed precursor with the proper amino terminal cleavage but lacking the carboxyl terminal cleavage of mature (mouse) EGF were calculated and compared with the experimentally derived values (Table 9).

The theoretical composition of the partially processed prepro EGF and the experimental composition of the sample are strikingly similar. Except for the amino acids serine and leucine, the amino acid composition of the sample matched that of the predicted partially processed precursor EGF. At the amino acids Glx, Pro, Cys and Tyr, where the theoretical compositions of an EGF tetramer and the partially processed precursor EGF were divergent, the experimental data were strikingly similar to data outlining the composition of a partially processed precursor but inconsistent with the amino acid composition predicted for an aggregated rat EGF. Moreover, at the amino acids Ala, Phe, and Lys, which are absent in mature rat EGF, the amino acid composition of the sample was almost identical to that of the predicted composition for a partially processed mouse pre-pro EGF molecule.

TABLE 5

Mitogenic Activity in Rat Tissues

| Tissue | Mitogenic Specific Activity (dpm/μg) | Relative Specific Activity (fold) | % Inhibition by Anti rat EGF AB |
|---|---|---|---|
| Submandibular | 20,000 | 100.00 | 92 |
| Prostate | | | |
| Ventral Lobe | 200 | 1.00 | 75 |
| Dorsolateral Lobe | 391 | 1.96 | 61 |
| Brain | 160 | .80 | — |
| Spleen | 121 | .61 | 0 |
| Heart | 95 | .48 | — |
| Kidney | 55 | .28 | — |
| Liver | 32 | .16 | — |

TABLE 6

Purification of EGF-Like Proteins by Protocol 2

| Purification Step | Total Protein (mg) | EGF RIA (μg) | % | Mitogenic Act. ($\times 10^{-7}$) (dpm) | % | Specific Act. (dpm/mg) |
|---|---|---|---|---|---|---|
| 1. Tris Extract (Prostate) | 288 | 6.3 | 100.0% | 30 | 100.0% | $1.0 \times 10^{-1}$ |
| 2. Applied to Immunoaffinity | 232 | 8.0 | 127.0% | 21 | 70.0% | $0.9 \times 10^{-1}$ |
| 3. Eluant from Immunoaffinity | N.D. | 4.5 | 71.4% | 14 | 47.0% | N.D. |
| 4. Flow Through Immunoaffinity | 284 | 1.4 | 22.0% | 8.8 | 30.0% | $3.0 \times 10^{-2}$ |
| 5. Heparin Seph. 0.1M | 112 | N.D. | | 5.3* | 17.6% | $4.7 \times 10^{-2}$ |
| 6. Heparin Seph. 0.8M | 52 | N.D. | | 3.8 | 12.6% | $7.3 \times 10^{-2}$ |
| 7. Heparin Seph. 2.0M | — | N.D. | | 1.1 | 3.6% | N.D. |

TABLE 7

Purification of 25-kDa Mitogen by Protocol 3

| Purification Step | Protein (mg) | Mitogenic Act (× 10⁻⁷ dpm) | % | Inhibition by Anti-Rat EGF AS |
|---|---|---|---|---|
| 1. (NH₄)₂SO₄ Extract | 728 | 10.0 | 100 | N.D. |
| 2. C.M. Flow Through | 620 | 0 | — | N.D. |
| 3. C.M. .15M NaCl | 140 | 0 | — | N.D. |
| 4. C.M. .5M NaCl | 10 | 1.6 | 16 | 85% |
| 5. Heparin Flow Through | N.D. | 1.0 | 10 | 85% |

TABLE 8

Comparison of 25-kDA Protein Isolated by Protocols 1, 2 and 3

| Purification Protocol | 25 kDa Mitogen | Inhibited by Anti-EGF Receptor AS | Inhibited by Anti-Rat EGF AS | Sequence Identity with Rat EGF |
|---|---|---|---|---|
| 1 | + | + | + | + |
| 2 | + | N.D. | + | + |
| 3 | + | N.D. | + | N.D. |

TABLE 9

Amino Acid Composition of EGF-Like Mitogens Isolated by Protocol 2

| AA | Exper. # of AAs | rat-mouse hybrid (rEGF + mC-term) Theor. # of AAs | (4x rEGF) Theor. # of AAs |
|---|---|---|---|
| ASX | 28.04 | 22.00 | 28.00 |
| THR | 10.40 | 7.00 | 4.00 |
| SER | 15.48 | 26.00 | 12.00 |
| GLX | 26.38 | 21.00 | 12.00 |
| PRO | 25.68 | 22.00 | 8.00 |
| GLY | 24.63 | 25.00 | 24.00 |
| ALA | 11.52 | 11.00 | 0.00 |
| CYS | 8.00 | 11.00 | 24.00 |
| VAL | 21.51 | 19.00 | 20.00 |
| MET | 2.90 | 5.00 | 4.00 |
| ILE | 6.87 | 6.00 | 8.00 |
| LEU | 11.65 | 20.00 | 8.00 |
| TYR | 10.65 | 10.00 | 20.00 |
| PHE | 4.81 | 1.00 | 0.00 |
| HIS | 6.64 | 9.00 | 4.00 |
| LYS | 8.86 | 8.00 | 0.00 |
| ARG | 8.71 | 12.00 | 16.00 |
|  | 232.74 | 235.00 | 192.00 |

Various other examples will be apparent to the person skilled in the art after reading the disclosure herein without departing from the spirit and scope of the invention and it is intended that all such examples be included within the scope of the appended claims.

What is claimed is:

1. A purified rat prostate tissue-derived growth factor having the following characteristics:
   (a) molecular weight of 25 kDa as determined by non-reduced sodium dodecylsulfate polyacrylamide gel electrophoresis,
   (b) an amino terminal sequence identical to the amino terminal sequence of FIG. 5A of the 6 kDa mature rat epidermal growth factor,
   (c) potent mitogenic activity against NRK cells without additional carboxy terminal processing to the mature 6 kDa epidermal growth factor species,
   (d) cross-reacts with antisera against rat epidermal growth factor, and
   (e) mitogenic activity is blocked by anti-epidermal growth factor receptor antisera.

2. The method of stimulating the growth of fibroblast cells comprising subjecting said cells to a growth stimulating amount of the prostate-derived growth factor of claim 1.

* * * * *